(12) United States Patent
Holmberg

(10) Patent No.: US 6,966,924 B2
(45) Date of Patent: Nov. 22, 2005

(54) ANNULOPLASTY RING HOLDER

(75) Inventor: William R. Holmberg, New Richmond, WI (US)

(73) Assignee: St. Jude Medical, Inc., St. Paul, MN (US)

( * ) Notice: Subject to any disclaimer, the term of this patent is extended or adjusted under 35 U.S.C. 154(b) by 160 days.

(21) Appl. No.: 10/222,157

(22) Filed: Aug. 16, 2002

(65) Prior Publication Data
US 2004/0034410 A1 Feb. 19, 2004

(51) Int. Cl.⁷ ................................. A61F 2/06
(52) U.S. Cl. ..................... 623/2.11; 606/1; 606/108
(58) Field of Search ............... 623/2.11, 2.36, 623/2.37, 900, 902, 904; 606/148, 108, 1; 128/898

(56) References Cited

U.S. PATENT DOCUMENTS

| 3,628,535 | A | * | 12/1971 | Ostrowsky et al. ......... 604/303 |
|---|---|---|---|---|
| 4,683,883 | A | | 8/1987 | Martin |
| 5,236,450 | A | | 8/1993 | Scott |
| 5,522,884 | A | | 6/1996 | Wright |
| 5,628,789 | A | | 5/1997 | Vanney et al. |
| 5,669,919 | A | | 9/1997 | Sanders et al. |
| 5,716,401 | A | | 2/1998 | Eberhardt et al. |
| 5,807,405 | A | | 9/1998 | Vanney et al. |
| 5,814,097 | A | | 9/1998 | Sterman et al. |
| 5,871,489 | A | | 2/1999 | Ovil |
| 5,906,642 | A | | 5/1999 | Caudillo et al. |
| 5,908,450 | A | | 6/1999 | Gross et al. |
| 5,972,030 | A | | 10/1999 | Garrison et al. |
| 5,984,959 | A | | 11/1999 | Robertson et al. |
| 6,019,790 | A | | 2/2000 | Holmberg et al. |
| 6,042,554 | A | | 3/2000 | Rosenman et al. |
| 6,110,200 | A | | 8/2000 | Hinnenkamp |
| 6,283,127 | B1 | | 9/2001 | Sterman |
| 6,283,993 | B1 | | 9/2001 | Cosgrove et al. |
| 6,319,280 | B1 | * | 11/2001 | Schoon ..................... 623/2.11 |
| 2001/0049558 | A1 | | 12/2001 | Liddicoat et al. |

FOREIGN PATENT DOCUMENTS

| WO | WO 00/59408 | 10/2000 |
|---|---|---|
| WO | WO 01/50985 | 7/2001 |

* cited by examiner

Primary Examiner—David J. Isabella
Assistant Examiner—Urmi Chattopadhyay
(74) Attorney, Agent, or Firm—Westman, Champlin & Kelly, P.A.; Hallie A. Finucane

(57) ABSTRACT

An annuloplasty ring holder includes a first member and a second member. The first and second members are configured to provide relative movement therebetween to engage an annuloplasty ring.

16 Claims, 4 Drawing Sheets

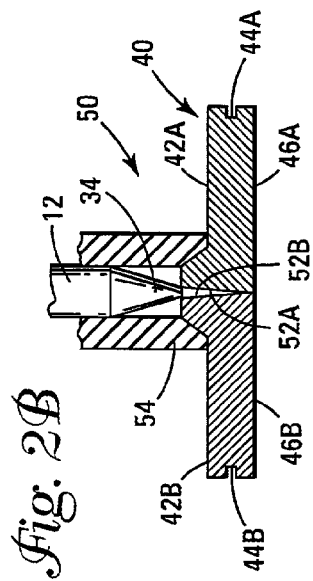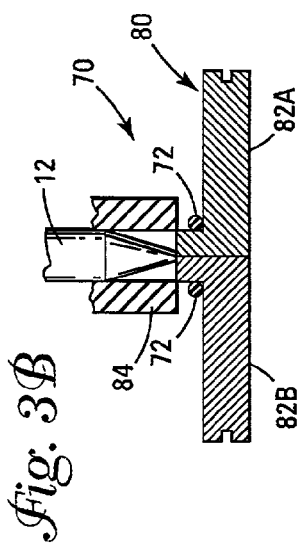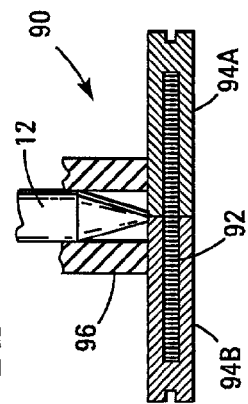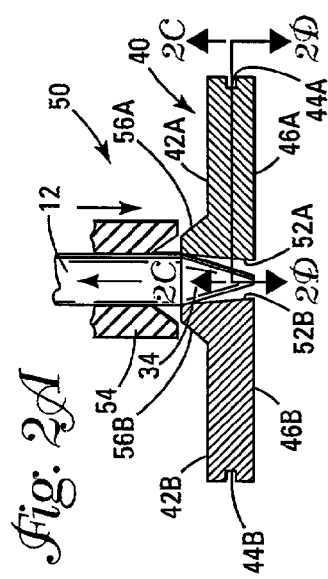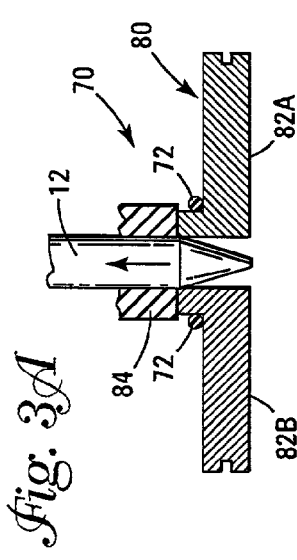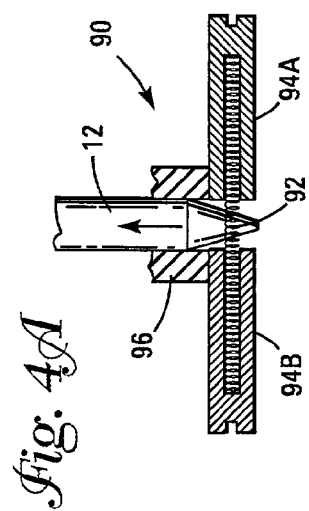

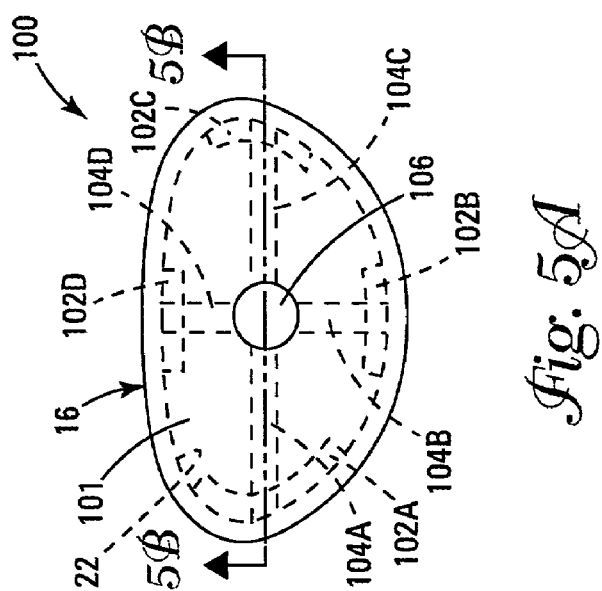
Fig. 5A
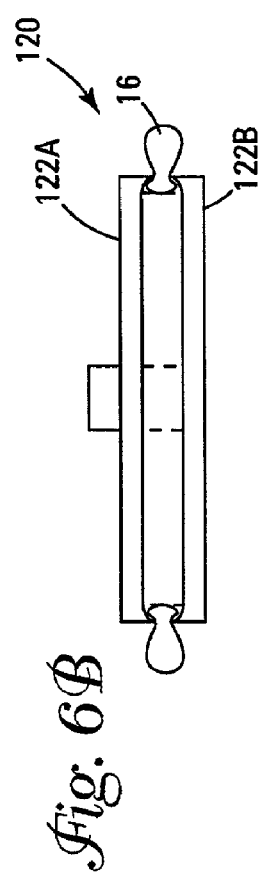
Fig. 6B
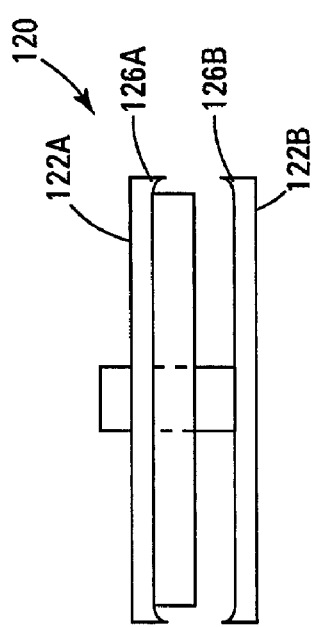
Fig. 6C
Fig. 6A

ANNULOPLASTY RING HOLDER

FIELD OF THE INVENTION

The present invention relates to annuloplasty rings. More specifically, the present invention relates to holders for holding annuloplasty rings.

BACKGROUND OF THE INVENTION

Annuloplasty ring holders are used for holding annuloplasty rings during implantation. Such holders are used for positioning, holding, supporting and presenting the annuloplasty ring during surgery.

Typically, annuloplasty rings are used to maintain the shape of the native valve after repair. In a diseased or damaged valve, when the valve closes, the annulus around the valve can change shape such that the valve leaflets do not completely close. This allows blood leakage in the reverse direction. The annuloplasty ring helps maintain the shape of the valve such that the leaflets close properly.

During surgery, the annuloplasty ring is held by an annuloplasty ring holder so that it can be positioned and manipulated by the surgeon. The holder is typically a D-shaped body to which the annuloplasty ring is sutured. See, for example U.S. Pat. No. 6,283,993, to Cosgrove et al. When using a holder of this type, after the annuloplasty ring has been positioned, the sutures are cut so that the holder can be removed.

The removal of the sutures which attach the annuloplasty ring to the holder can be cumbersome and time consuming. Cutting the sutures can also cause damage to the annuloplasty ring. Care must be taken to ensure that pieces of the suture remain attached to the holder and are not left in the patient. The drag from the suture can make it difficult to remove the ring from the holder. Further, the retention sutures can be captured by the sutures used to implant the ring, thereby creating great difficulty in removing the ring from the holder. In addition, it is difficult, if not impossible, to reattach the annuloplasty ring to the holder in such a configuration.

SUMMARY OF THE INVENTION

An annuloplasty ring holder includes at least one member. Movement of the moveable member selectively captures an annuloplasty ring on the holder.

BRIEF DESCRIPTION OF THE DRAWINGS

FIG. 2A is a side exploded cross-sectional view of an annuloplasty ring holder including a collar.

FIG. 2B is a side cross-sectional view of the annuloplasty ring holder of FIG. 2A.

FIG. 3A is a side cross-sectional view of an annuloplasty ring holder in accordance with another embodiment.

FIG. 3B is a side cross-sectional view of the annuloplasty ring holder of FIG. 3A with a handle partially removed.

FIG. 4A is a side cross-sectional view of an annuloplasty ring holder in accordance with another embodiment.

FIG. 4B is a side cross-sectional view of the annuloplasty ring holder of FIG. 4A with a handle partially removed.

FIG. 5A is a top plan view of an annuloplasty ring holder including more than two members in accordance with another embodiment.

FIG. 6A is a top plan view of an annuloplasty ring holder configured to grip an annuloplasty ring.

FIG. 6B is a side view of the annuloplasty ring holder of FIG. 6A shown gripping an annuloplasty ring.

FIG. 6C is a side exploded view of the annuloplasty ring holder of FIG. 6B.

DETAILED DESCRIPTION OF THE PREFERRED EMBODIMENTS

Figure 1:
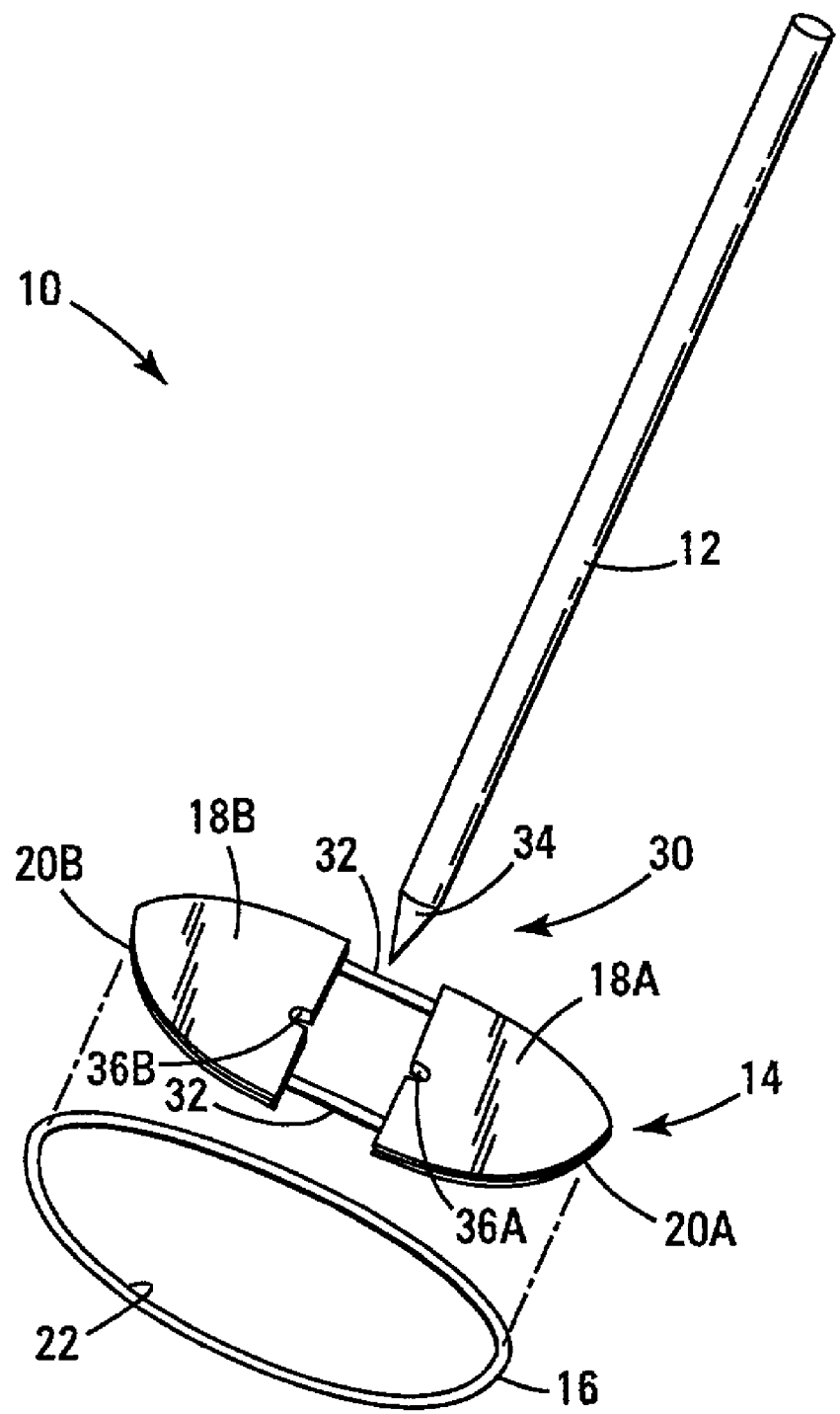
FIG. 1 is an exploded perspective view of an annuloplasty ring holder assembly in accordance with one embodiment of the present invention.

FIG. 1 is an exploded perspective view of an annuloplasty ring holder assembly 10 which includes an elongated member, such as handle 12 and an annuloplasty ring holder 14. Holder 14 is configured to hold an annuloplasty ring 16 during implantation. In one aspect, an annuloplasty ring 16 is a substantially rigid ring and the holders depicted in FIGS. 1–4 hold the ring using an interference fit and do not rely on placing the ring under tension. These configurations do not cause deformation of the ring which can occur if the ring is placed under tension. Ring holder 14 includes first and second body members 18A,18B. Members 18A,18B include annuloplasty ring engaging surfaces 20A,20B, respectively, which are configured to engage interior surface 22 of annuloplasty ring 16. Ring 16 should be a closed (i.e., complete) ring, or a semi-rigid or rigid open ring such that ring 16 is held securely against surfaces 20A,20B.

The present invention includes a spreading mechanism 30 coupled between members 18A,18B configured to spread members 18A,18B apart and generally in the plane of the ring 16. A number of spreading mechanisms are illustrated herein, however, the present invention is not limited to these configurations. In the embodiment of FIG. 1, spreading mechanism 30 includes guides 32 which are configured to guide members 18A,18B. A tip 34 on handle 12, or other insertion mechanism, such as forceps, is received in openings 36A and 36B of members 18A,18B, respectively. Tip 34 is angled and forces members 18A,18B apart, when inserted.

In the embodiments illustrated in FIGS. 1–4, the moveable members move in the same plane with respect to each other. The engaging surfaces have a full or partial lip on the proximal side and only a partial lip on the distal side. This is illustrated and discussed in more detail with respect to FIGS. 2C and 2D. The partial distal lip is configured to engage the annuloplasty ring 16 when the members are spread apart and to release or free the ring 16 when the members are brought together. The partial lip on the distal side of the members is positioned so that the partial lip extends in the direction of movement of the members. In one embodiment, when the moveable members are moved apart, the annuloplasty ring 16 is grasped using an interference fit and positioned against the distal partial lips. The annuloplasty ring 16 is not placed under tension which could lead to deformation of the ring.

FIG. 1 provides a simple diagram which illustrates operation of the present invention. In various general aspects, the present invention includes at least two body members 18A, 18B which are spread apart by some type of spreading mechanism 30 such that when engaged, surfaces 20A,20B engage interior surface 22 of ring 16. The spreading mechanism 30 can be distributed between a number of different components and is not limited to the particular configurations shown herein. As used herein, the spreading mechanism can include features which draw two members together in addition to the spreading function. The spreading of the two members is a relative movement. For example, in FIG. 1, the spreading mechanism includes the configuration of tip 34 which fits into openings 36A and 36B to thereby cause displacement of both members 18A,18B as they slide along guides 32. As is used herein, spreading can also mean that one of the members is held stationary while the other member moves apart.

Figure 2C:
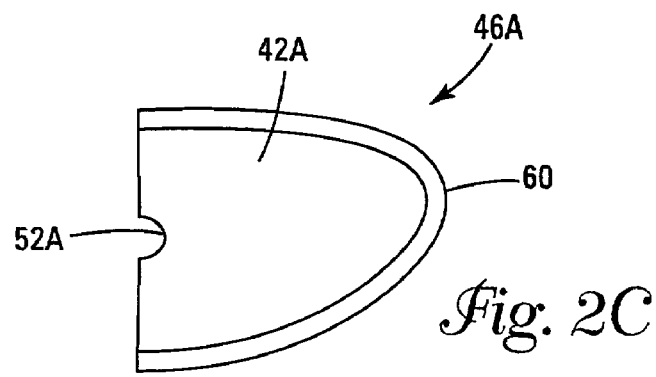
FIG. 2C is a cross-sectional view showing a proximal lip of a moveable member taken along the line 2C—2C shown in FIG. 2A.

FIG. 2A is a cross-sectional exploded side view and FIG. 2B is a cross-sectional side view of another embodiment of the present invention. In FIGS. 2A, 2B, annuloplasty ring holder 40 includes members 42A and 42B which have annuloplasty ring engaging surfaces 44A and 44B, respectively. Surfaces 44A,44B are formed in flanges 46A and 46B, respectively, which extend along members 42A and 42B and defined between lips 60 and 62 (shown in FIGS. 2C and 2D). Flanges 46A,46B are configured to hold annuloplasty ring 16 shown in FIG. 1. In the embodiment of FIGS. 2A, 2B, a spreading mechanism 50 includes tapered side walls 52A and 52B formed, respectively, in members 42A and 42B configured to receive tapered tip 34 of handle 12. As illustrated in FIG. 2A, as tip 34 is urged against sides walls 52A and 52B, members 42A and 42B are spread apart. A collar 54 fits around tapered lips 56A and 56B of members 42A and 42B, respectively, to draw members 42A and 42B together and thereby release annuloplasty ring 16. In one embodiment, lips 56A and 56B are not tapered. Collar 54 can be tapered such that as handle 12 is moved in an upward direction as illustrated by the arrow in FIG. 2A, collar 54 moves in a downward direction, thereby drawing members 42A and 42B together. Collar 54 can be formed of, for example, a rigid or elastic material such as metal, rigid polymer, rubber, etc.

Figure 2D:
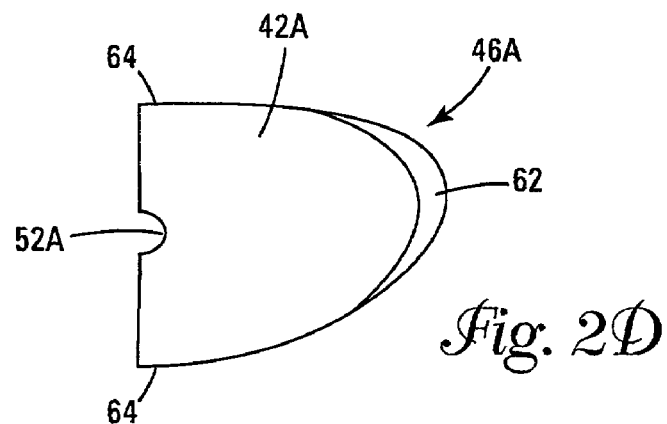
FIG. 2D is a cross-sectional view showing a partial distal lip of a moveable member taken along the line 2D—2D shown in FIG. 2A.

FIG. 2C is a cross-sectional view of member 42A as viewed toward a proximal lip 60 and is indicated by line 2C—2C shown in FIGS. 2A. Proximal lip 60 on flange 46A is similar on member 42B and extends at least partially around the circumference of member 42A and is configured to capture annuloplasty ring 16. FIG. 2D is a cross-sectional view of member 42A taken along the line labeled 2D—2D shown in FIG. 2A. FIG. 2D illustrates partial distal lip 62 which extends from member 42A in a direction parallel with a direction of movement of member 42A. As illustrated in FIG. 2D, the partial lip 62 does not extend along inline sides 64 of member 42A. Member 42B has a similar lip configuration. With the lip configuration illustrated in FIGS. 2C and 2D, the ring 16 can be captured between proximal lip 60 and partial distal lip 62 when members 42A and 42B are spread apart. However, when members 42A and 42B are brought together, the ring 16 can pass over distal lip 62 and is thereby released from the holder 40. For this configuration, it is not necessary to place significant tension on ring 16 which could cause deformation of the ring 16.

FIGS. 3A and 3B show another embodiment including a spreading mechanism 70 and an elastic O-ring 72 configured to draw members 82A and 82B of holder 80 together as illustrated in FIG. 3B. Collar 84 can optionally be used to press around members 82A and 82B as handle 12 is removed, similar to the embodiment in FIG. 2. Collar 84 can be held to assist in removing the handle 12 and drawing members 82A and 82B together to release ring 16 or can be used during a reinsertion process of the handle, for instance, to manipulate ring 16.

FIGS. 4A and 4B show another embodiment in which spreading mechanism 90 includes a spring 92 which spans members 94A and 94B. Spring 92 is configured to draw members 94A,94B together as illustrated in FIG. 4B when handle 12 is removed thereby releasing ring 16. Collar 96 shown in FIGS. 4A and 4B can be grasped by a surgeon during implantation and held as handle 12 is inserted or removed from the holder.

Figure 5B:
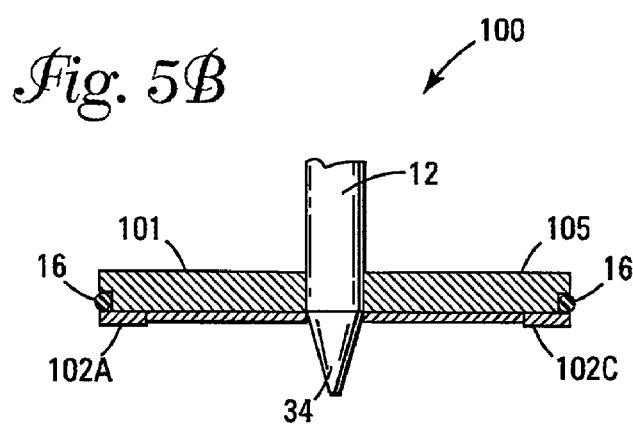
FIG. 5B is a cross-sectional view of the holder of FIG. 5A taken along line 5B—5B in FIG. 5A.

FIG. 5A is a top plan view and FIG. 5B is a side cross-sectional view taken along the line labeled 5B—5B in FIG. 5A of a holder 100 in accordance with another embodiment. Shown in phantom in FIG. 5A are members 102A, 102B, 102C and 102D which include surfaces which are configured to capture annuloplasty ring 16. Proximal and distal lips can be provided to capture the ring 16 such that the ring is held against holder 100 without placing the ring under tension. Alternatively, members 102A,B,C and D are distal lips which slide out from the holder 100 to thereby capture ring 16 against a proximal lip, such as that shown in FIG. 2C. Members 102A,B,C and D are coupled, respectively, to spokes 104A, 104B, 104C and 104D of spreading mechanism 101 which extend to a central opening 106. Although spokes are shown, other radial pieces could be used such as plates, etc. Opening 106 is configured to receive tip 34 of handle 12. Tip 34 presses against spokes 104A,B,C and D thereby urging the members 102A,B,C and D, respectively, underneath ring 16. Spokes 104A,B,C and D are preferably drawn together such that members 102A, B,C and D do not engage the ring 16, allowing the ring to come off the holder. When handle 12 (not shown in FIGS. 5A,B) is inserted into opening 106, the spokes 104A,B,C and D are urged radially outward such that members 102A, B,C and D, along with a proximal lip 105, capture ring 16 therebetween. Although four members are shown in FIG. 5A, any number of members can be used, including two or more.

FIG. 6A is a top plan view, FIG. 6B is a side view and FIG. 6C is a side exploded view of an annuloplasty ring holder 120 in accordance with another embodiment. Annuloplasty ring holder 120 includes a first body member 122A and a second body member 122B having an opening 124 formed therethrough which is configured to receive a handle. Opening 124 illustrates an embodiment of a square opening to prevent members 122A,122B from rotating with respect to each other. Other shapes such as a triangular shape, etc. can be employed. Members 122A and 122B include outer circumferential opposed jaws 126A and 126B, respectively, which are configured to grip annuloplasty ring 16 as illustrated in FIG. 6B and which extend partially or completely around the circumference of members 122A and 122B. Jaws 126A and 126B provide another example of ring engaging surfaces configured to engage a surface of an annuloplasty ring. Members 122A,B can clamp together and thereby grip ring 16. When members 122A,B are released, as illustrated in FIG. 6C, ring 16 is released. The handle engages member 122B allowing members 122A and 122B to come together. This can be, for example, by providing the handle with a releasable clip or by other means. By pulling back on the handle or otherwise actuating the handle, the members 122A and 122B can move apart to the position shown in FIG. 6C. Other mechanisms include a threaded handle, a spring loaded handle with a clip, a pushpin or a push button. For example, if handle 12 engages member 122B, the handle can be used to pull member 122B toward member 122A. A spring between members 122A and 122B along with a push button, clip, or other device, can cause member 122A to move away from member 122B, thereby releasing the annuloplasty ring 16. With a threaded collar attached to member 122A, a threaded shaft on handle 12 can be used to spread members 122A and 122B apart. These are example configurations and the present invention is not limited to these particular embodiments. The configuration shown in FIGS. 6A, 6B and 6C does not place the ring 16 under tension and is well suited for partial or flexible annuloplasty rings.

In the embodiment illustrated in FIGS. 6A, 6B and 6C, the body members move in an axial direction, whereas in FIGS. 1–5, the members are illustrated as moving in a planar direction.

The various holder and handle components of the invention can be fabricated using an appropriate biocompatible material. Such materials include, but are not limited to, stainless steel, rigid polymers such as polyacetal resin (DELRIN) or polysulfone (Radel), titanium, rubber, etc.

In one aspect two or more body members with at least one capable of moving relative to the annuloplasty ring to grip or otherwise secure the annuloplasty ring. The holders herein do not require the sutures for attaching the ring to the holder seen in typical prior art designs. Additionally, the holder of the present invention can be easily reattached to the annuloplasty ring, unlike a design which uses sutures, by reversing the removal process.

Although the present invention has been described with reference to preferred embodiments, workers skilled in the art will recognize that changes may be made in form and detail without departing from the spirit and scope of the invention. For example, the tip of the handle can be secured to the members and does not need to be a separate component. The tip can be a separate component which is attached to the holder. The handle can separately attached to the tip prior to surgery. The handle with a tip can be preassembled to the holder as a disposable item. To ensure that the holders of the present invention do not apply tension to the ring, the holders are preferably provided in various sizes to match the various sizes of annuloplasty rings which are available. In one aspect, the handle 12 comprises any type of elongate member including forceps.

What is claimed is:

1. An annuloplasty ring holder, comprising:
    a first member including a first annuloplasty ring engaging surface configured to receive an annuloplasty ring;
    a second member generally opposed to the first member, the second member including a second annuloplasty ring engaging surface configured to receive the annuloplasty ring;
    first and second partial distal lips which extend partially around a distal edge of the engaging surfaces of the respective first and second members; and
    a spring member configured to draw the first and second members together and thereby release the annuloplasty ring;
    wherein the first member is moveable relative to the second member, whereby the first and second partial distal lips cooperate to releasably hold the annuloplasty ring.

2. The annuloplasty ring holder of claim 1 wherein the first and second members are configured to move generally along a plane defined by the annuloplasty ring.

3. The annuloplasty ring holder of claim 1 wherein the first and second annuloplasty ring engaging surfaces are configured to abut an interior surface of the annuloplasty ring without significantly deforming the ring.

4. The annuloplasty ring holder of claim 1 wherein the first and second members include an opening formed therein which is configured to receive a tip of an elongated member, the tip configured to spread the members apart.

5. The annuloplasty ring holder of claim 1 wherein the first and second annuloplasty ring engaging surfaces are defined by the partial distal lips and by a proximal lip configured to engage the interior surface of the annuloplasty ring.

6. The annuloplasty ring holder of claim 1 including at least one guide which extends between first and second members configured to guide relative movement therebetween.

7. The annuloplasty ring holder of claim 1 wherein the spring member comprises a collar configured to draw the first and second members together and thereby release the annuloplasty ring.

8. The annuloplasty ring holder of claim 1 wherein the spring member comprises an O-ring.

9. The annuloplasty ring holder of claim 1 wherein the spring member comprises a spring which extends between the first and second members.

10. A method for holding an annuloplasty ring, comprising:
    placing a first member having a first annuloplasty ring engaging surface and a second member having a second annuloplasty ring engaging surface adjacent the annuloplasty ring, the first and second annuloplasty ring engaging surfaces defined between a proximal lip and a partial distal lip, the partial distal lip extending partially around an outer circumference of the members;
    providing relative movement between the first arid second members whereby a surface of the annuloplasty ring is secured in the first and second annuloplasty ring engaging surfaces between the proximal lip and the partial distal lip; and
    drawing the first and second members together using a spring member and thereby releasing the annuloplasty ring.

11. The method of claim 10 wherein providing relative movement comprises spreading the first and second members apart and generally in a plane of the annuloplasty ring.

12. The method of claim 10 wherein providing relative movement comprises inserting an elongated member into the first and second members.

13. The method of claim 10 wherein providing relative movement comprises moving the partial distal lip generally in a plane parallel with a plane of the annuloplasty ring.

14. The method of claim 10 wherein the spring member comprises a spring.

15. The method of claim 10 wherein the spring member comprises an O-ring.

16. The method of claim 10 wherein providing relative movement comprises receiving a tip of an elongate member between the first and second members to thereby spread the first and second members apart.

* * * * *